United States Patent [19]

Tomita et al.

[11] Patent Number: 4,540,802

[45] Date of Patent: Sep. 10, 1985

[54] EPOXY RESIN AND PROCESS FOR PREPARING THE SAME

[75] Inventors: Haruo Tomita; Kazuya Yonezawa, both of Kobe, Japan

[73] Assignee: Kanegafuchi Kagaku Kogyo Kabushiki Kaisha, Osaka, Japan

[21] Appl. No.: 491,226

[22] Filed: May 3, 1983

[30] Foreign Application Priority Data

May 31, 1982 [JP] Japan ................................. 57-93446

[51] Int. Cl.³ ................. C07D 303/26; C07D 303/27; C07D 303/16; C07D 301/30
[52] U.S. Cl. .................... 549/557; 549/515; 549/517
[58] Field of Search ............................. 549/515, 557

[56] References Cited

U.S. PATENT DOCUMENTS

| | | | |
|---|---|---|---|
| 3,372,142 | 3/1968 | Smith | 549/517 |
| 4,284,573 | 8/1981 | Arnett et al. | 549/517 |
| 4,373,073 | 2/1983 | Wojtech et al. | 549/517 |

OTHER PUBLICATIONS

Chemical Abstracts, vol. 94:209461m (1981).

Primary Examiner—Norma S. Milestone
Attorney, Agent, or Firm—Antonelli, Terry & Wands

[57] ABSTRACT

An epoxy resin of the general formula:

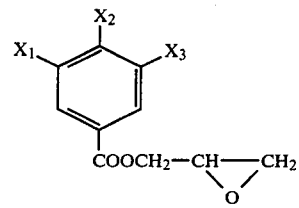

wherein $X_1$ and $X_2$ are —OH or

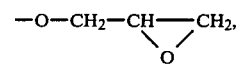

and $X_3$ is —OH,

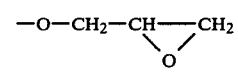

or a group of the general formula:

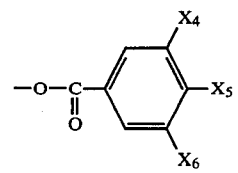

in which $X_4$, $X_5$ and $X_6$ are —OH or

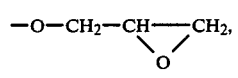

provided that at least one of $X_1$ to $X_6$ is

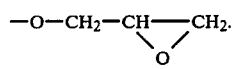

The epoxy resin produced by reaction of gallic acid or tannic acid with an epihalohydrin in the presence of a phase transfer catalyst and reacting the obtained reaction mixture with an aqueous alkali solution.

4 Claims; 2 Drawing Figures

EPOXY RESIN AND PROCESS FOR PREPARING THE SAME

BACKGROUND OF THE INVENTION

The present invention relates to a polyglycidyl compound useful as an epoxy resin and a process for the preparation thereof, and more particularly to an epoxy resin obtained from gallic acid or tannic acid by introducing glycidyl groups to hydroxyl and carboxyl group of gallic or tannic acid.

Hitherto, various polyglycidyl compounds have been prepared by reacting polyhydric phenols, carboxylic acids or amines with epihalohydrins to introduce glycidyl groups, and have been employed as epoxy resins. It is expected that polyglycidyl compounds obtained by using aromatic polyhydroxycarboxylic acids as starting materials have characteristics useful as epoxy resins. Gallic acid and tannic acid which is the condensate of gallic acid, are known as aromatic polyhydroxycarboxylic acids which are abundantly present in nature and are easily obtainable.

On the other hand, introduction of glycidyl groups to compounds having both of carboxyl group and phenolic hydroxyl group by the reaction thereof with epihalohydrins has not been easy in general, since the produced glycidyl ester moiety is subject to hydrolysis owing to an aqueous alkali solution.

An object of the present invention is to provide a novel epoxy resin.

A further object of the invention is to provide a novel epoxy resin derived from gallic acid or tannic acid present abundantly in nature and easily obtainable.

Another object of the invention is to provide a process for preparing an epoxy resin with ease in high yields from gallic acid or tannic acid.

These and other objects of the present invention will become apparent from the description hereinafter.

SUMMARY OF THE INVENTION

In accordance with the present invention, there is provided an epoxy resin having the general formula:

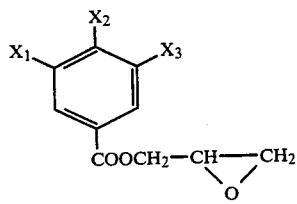

wherein $X_1$ and $X_2$ are —OH or

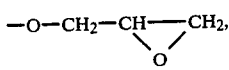

and $x_3$ is —OH,

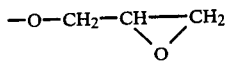

or a group of the general formula:

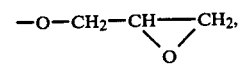

in which $X_4$, $X_5$ and $X_6$ are —OH or

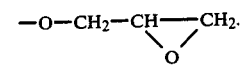

provided that at least one of $X_1$ to $X_6$ is $$-O-CH_2-CH\underset{O}{\overset{}{\diagup\!\!\!\diagdown}}CH_2.$$

DETAILED DESCRIPTION

Figure 1:
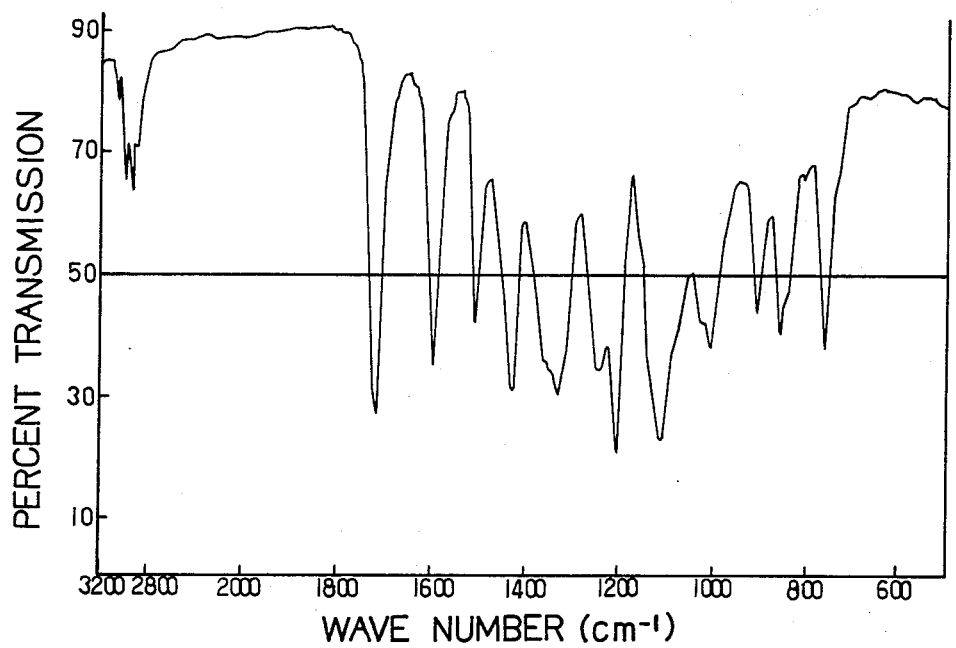
FIGS. 1 and 2 are infrared absorption spectrums of the epoxy resins of the present invention.

Gallic acid or tannic acid is used as a starting material in the present invention. Gallic acid is represented by the following structural formula:

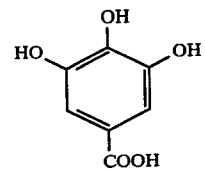

Tannic acid is a condensate of gallic acid and is represented by the following structural formula:

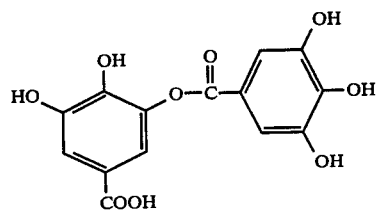

The epoxy resin of the present invention is a, polyglycidyl compound obtained by introducing glycidyl groups to carboxyl group and at least one phenolic hydroxyl group of the above-mentioned hydroxycarboxylic acid with an epihalohydrin. The thus obtained polyglycidyl compound can be cured with a generally known curing agent such as a polyamine or an acid anhydride to provide a cured product having a high deflection temperature, and is useful as an epoxy resin.

As mentioned before, the production of a polyglycidyl compound by the reaction of a hydroxycarboxylic acid and an epihalohydrin has not been easy, because the produced glycidyl ester moiety is subject to hydrolysis owing to an alkali. This problem has been solved by the process of the present invention. The process of the present invention is characterized in that gallic acid or tannic acid is reacted with an epihalohydrin in the presence of a phase transfer catalyst and in the substantial absence of water, thereby causing addition reaction of the epihalohydrin to carboxyl group and at least one phenolic hydroxyl group to occur. After the addition reaction, the reaction mixture is reacted with an aqueous solution of an alkali metal hydroxide in the presence of a phase transfer catalyst to produce an epoxy resin. The process of the present invention will be explained in detail.

In the first step of the process of the present invention, the addition reaction of an epihalohydrin to hydroxyl and carboxyl groups of gallic or tannic acid is conducted by reacting gallic or tannic acid with the epihalohydrin in the presence of a phase transfer catalyst. The reaction may be carried out with or without employing a solvent such as toluene, benzene or chlorobenzene. A part of the halohydrin ether or halohydrin ester moiety formed by the addition reaction is converted into glycidyl ether or glycidyl ester moiety owing to excess epihalohydrin.

Epichlorohydrin, epibromohydrin and epiiodohydrin are employed as an epihalohydrin. The epihalohydrin is employed in an equimolar or more amount based on the total of carboxyl group and hydroxyl groups of gallic or tannic acid, preferably in an amount of 3 to 10 times the molar amount of the total of carboxyl and hydroxyl groups of gallic or tannic acid.

The addition reaction is carried out at a temperature of 50° to 110° C. preferably 90° to 100° C. The reaction time varies depending on the reaction temperature. For instance, in case of carrying out the reaction at 100° C., it is necessary to carry out the reaction for more than 30 minutes, but the reaction for a too long time is not desirable due to production of a high molecular weight compound.

The presence of the phase transfer catalyst is essential for the addition reaction in the first step of the process of the invention. If the phase transfer catalyst is not present, the addition reaction does not proceed. The phase transfer catalyst is employed in an amount of 0.1 to 50% by mole, preferably 1 to 10% by mole, based on gallic or tannic acid used. Phase transfer catalysts generally known are usable in the present invention. Representative examples of the phase transfer catalysts are, for instance, quaternary ammonium salts such as tetrabutylammonium bromide, trioctylmethylammonium chloride and benzyltriethylammonium chloride. quaternary phosphonium salts such as tetraphenylphosphonium chloride and triphenylmethylphosphonium chloride, and quaternary arsonium salts.

In the second step of the process of the present invention, dehydrohalogenation of the halohydrin ether and halohydrin ester moieties of the reaction product obtained in the first step is conducted by adding an aqueous solution of an alkali metal hydroxide to the reaction mixture obtained in the first step or the reaction mixture from which the unreacted epihalohydrin is removed by distilling away, whereby the desired polyglycidyl compound having glycidyloxycarbonyl group and at least one glycidyloxy group is produced. Usually, the reaction is conducted by vigorously agitating the reaction mixture obtained in the first step and an aqueous alkali solution. Upon carrying out the dehydrohalogenation, the phase transfer catalyst may be added to the reaction system. The additional amount of the phase transfer catalyst is from 0.1 to 50% by mole, preferably 1 to 10% by mole, based on the total of carboxyl group and hydroxyl groups of the employed gallic or tannic acid.

The aqueous solution of an alkali metal hydroxide is employed in a concentration of 5 to 50% by weight. The amount of the alkali metal hydroxide is not less than 1 time, preferably 1.3 to 2.5 times, the molar amount of the total of hydroxyl groups and carboxyl group of the gallic or tannic acid employed as a starting material.

The reaction temperature and the reaction time in the second step of the process of the invention are selected so that the dehydrohalogenation reaction sufficiently proceeds and moreover the alkali hydrolysis of the ester linkage is prevented. Usually, the reaction is conducted at a temperature of 20° to 30° C. for 20 minutes to 2 hours with agitation.

In the second step of the process of the invention, the phase transfer catalyst serves to accelerate the dehydrohalogenation reaction. Therefore, the dehydrohalogenation of the halohydrin ether and halohydrin ester moieties by an aqueous alkali solution is completed at a low temperature in a short period of time and the loss of the product owing to hydrolysis of the glycidyl ester moiety is decreased.

After the completion of the dehydrohalogenation reaction, the reaction mixture is separated into two layers by allowing to stand. The desired polyglycidyl compound is recovered by removing the aqueous layer from the reaction mixture and washing the residual layer with water several times, and if necessary, further distilling away the unreacted epihalohydrin under reduced pressure.

The thus obtained polyglycidyl compound is useful as an epoxy resin. The epoxy resin of the present invention has an epoxy equivalent of 130 to 150. The infrared absorption spectrum of this epoxy resin indicates that all carboxyl groups are converted into glycidyloxycarbonyl group, and from the epoxy equivalent value it is clear that at least one phenolic hydroxyl group is converted into glycidyloxy group. The epoxy resin of the present invention is a high viscous liquid at ordinary temperature and has a light yellow color. The epoxy resin of the invention can be cured by employing generally known curing agents such as polyamines and acid anhydrides, and the curing rate thereof is larger than bisphenol A type epoxy resin. The heat deflection temperature of the cured product obtained by curing the epoxy resin of the invention with 3,6-endomethylene-1,2,3,6-tetrahydromethylphthalic anhydride is not less than 180° C., and is higher than that of the cured product of diglycidyl ether of bisphenol A by not less than 30° C. Thus, the polyglycidyl compounds of the present invention derived from gallic acid or tannic acid have excellent characteristics as epoxy resins.

The present invention is more specifically described and explained by means of the following Examples, in which all parts are by weight. It is to be understood that the present invention is not limited to the Examples, and various changes and modifications may be made in the invention without departing from the spirit and scope thereof.

Example 1

A mixture of 3.76 g. (20 millimoles) of gallic acid (monohydrate), 29.6 g. (320 millimoles) of epichlorohydrin and 0.23 g. (1 millimole) of benzyltriethylammonium chloride was agitated at 100° C. for 1 hour in a flask equipped with a reflux condenser. The reaction mixture was cooled to 30° C., and thereto were added 32 g. of a 20% by weight aqueous solution of sodium hydroxide (160 millimoles of sodium hydroxide) and 0.46 g. (2 millimoles) of benzyltriethylammonium chloride. The mixture was vigorously agitated at 30° C. for 90 minutes. The reaction mixture was allowed to stand to separate into two layers. The aqueous layer was removed. The residual layer was washed with water twice, and the unreacted epichlorohydrin was distilled away at 100° C. under reduced pressure (3 mmHg) to give 3.11 g. of a high viscous liquid.

The infrared absorption spectrum of the product is shown in FIG. 1. In the spectrum there are observed an absorption for ester at 1,715 cm.$^{-1}$ and absorptions for terminal epoxy group at 3,050 and 905 cm.$^{-1}$ The product had an epoxy equivalent of 137 measured by a hydrochloric acid-dioxane method. The calculated value for the epoxy equivalent of an epoxy resin derived from gallic acid by introducing glycidyl groups to carboxyl group and two hydroxyl groups is 113.

To 100 parts of the thus obtained epoxy resin were added 113 parts of 3,6-endomethylene-1,2,3,6-tetrahydromethylphthalic anhydride (commercially available under the commercial name "Methylhimic Anhydride" made by Hitachi Chemical Company. Ltd.) and 2 parts of benzyldimethylamine, and the epoxy resin was cured at 100° C. for 3 hours and then at 150° C. for 15 hours. The cured product had a heat deflection temperature of 184° C. (ASTM D-648, 18.54 kg./cm. load). For comparison, a mixture of 100 parts of a diglycidyl derivative of bisphenol A (epoxy resin commercially available under the commercial name "Epikote 828" made by Shell International Chemicals Corp.), 84.7 parts of Methylhimic Anhydride and 2 parts of benzyldimethylamine was cured under the same condition as above. The cured product had a heat deflection temperature of 147° C.

Example 2

A mixture of 3.76 g. (20 millimoles) of gallic acid (monohydrate), 29.6 g. (320 millimoles) of epichlorohydrin and 0.23 g. (1 millimole) of benzyltriethylammonium chloride was agitated at 100° C. for 1 hour in a flask equipped with a reflux condenser. The reaction mixture was cooled to 20° C., and thereto were added 32 g. of a 20% by weight aqueous solution of sodium hydroxide and 0.46 g. (2 millimoles) of benzyltriethylammonium chloride. The mixture was vigorously agitated at 20° C. for 1 hour, and thereafter the reaction mixture was treated in the same manner as in Example 1 to give 4.53 g. of a high viscous liquid. The infrared spectrum of the product agreed with that obtained in Example 1. The epoxy equivalent of the product was 142.

To 100 parts of the thus obtained epoxy resin were added 110 parts of Methylhimic Anhydride and 2 parts of benzyldimethylamine, and the mixture was cured under the same condition as in Example 1. The heat deflection temperature of the cured product was 181° C.

Example 3

A mixture of 3.76 g. (20 millimoles) of gallic acid (monohydrate), 29.6 g. (320 millimoles) of epichlorohydrin and 0.11 g. (0.5 millimole) of benzyltriethylammonium chloride was agitated at 100° C. for 2 hours in a flask equipped with a reflux condenser. The unreacted epichlorohydrin was removed from the reaction mixture by distilling away at 100° C. under reduced pressure (3 mmHg) to give 9.22 g. of a viscous liquid.

The viscous liquid was dissolved in 50 ml. of methylene chloride, and to the solution were added 0.46 g. (2 millimoles) of benzyltriethylammonium chloride and 18 g. of a 20% by weight aqueous solution of sodium hydroxide (90 millimoles of sodium hydroxide). The mixture was vigorously agitated at 20° C. for 30 minutes. After allowing the reaction mixture to stand and removing the aqueous layer, the methylene chloride layer was washed with water twice and methylene chloride was distilled away at 100° C. under reduced pressure (3 mmHg) to give 5.34 g. of a high viscous liquid. The product had an epoxy equivalent of 151. The infrared spectrum of the product almost agreed with those obtained in Examples 1 and 2.

To 100 parts of the thus obtained epoxy resin were added 103 g. of Methylhimic Anhydride and 2 parts of benzyldimethylamine, and the mixture was cured at 100° C. for 3 hours and then at 150° C. for 15 hours. The heat deflection temperature of the cured product was 186° C.

Example 4

A mixture of 3.42 g. (10 millimoles) of tannic acid, 29.6 g. (320 millimoles) of epichlorohydrin and 0.23 g. (1 millimole) of benzyltriethylammonium chloride was agitated at 100° C. for 2 hours in a flask equipped with a reflux condenser. The reaction mixture was cooled to 20° C., and thereto were added 16 g. of a 20% by weight aqueous solution of sodium hydroxide and 0.23 g. (1.0 millimole) of benzyltriethylammonium chloride. The mixture was vigorously agitated at 20° C. for 30 minutes, and thereafter the reaction mixture was treated in the same manner as in Example 1 to give 6.33 g. of a brown high viscous liquid.

Figure 2:
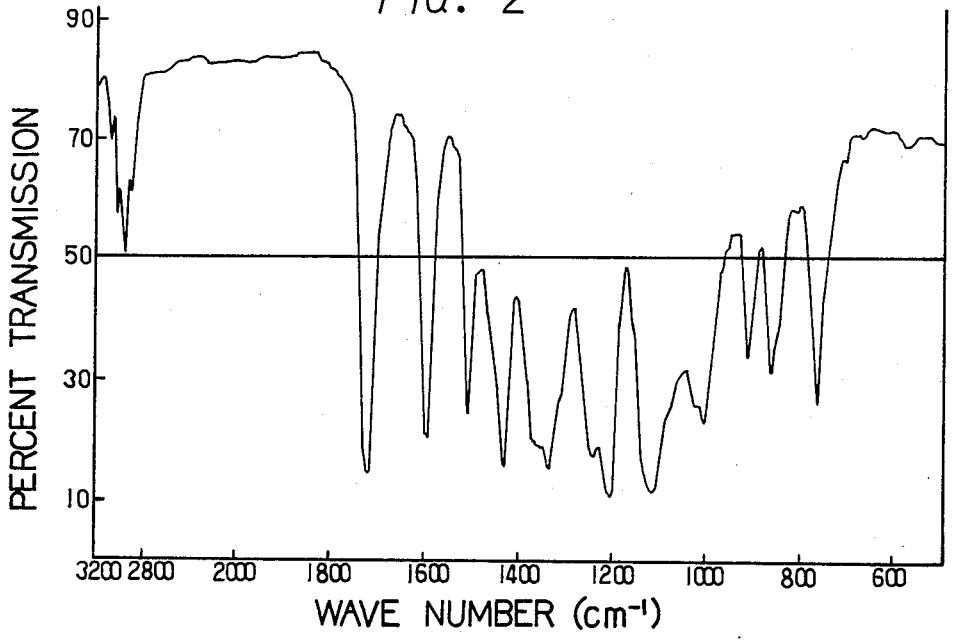

The infrared absorption spectrum of the product is shown in FIG. 2. In the spectrum, there are observed an absorption for ester at 1,715 cm.$^{-1}$ and absorptions for terminal epoxy group at 3,050 and 905 cm.$^{-1}$. The epoxy equivalent of the product measured by a hydrochloric acid-dioxane method was 160.

Comparative Example 1

A mixture of 3.76 g. (20 millimoles) of gallic acid (monohydrate) and 29.6 g. (320 millimoles) of epichlorohydrin was agitated at 100° C. for 2.5 hours in a flask equipped with a reflux condenser. The substance recovered by distilling away epichlorohydrin from the reaction mixture at 100° C. under reduced pressure (3 mmHg) was gallic acid used as a starting material.

In addition to the ingredients used in the Examples, other ingredients can be used in the Examples as set forth in the specification to obtain substantially the same results.

What we claim is:

1. An epoxy resin produced by reaction of gallic acid and an epihalohydrin in the presence of a phase transfer catalyst and in the substantial absence of water at 50° to 110° C., with the epihalohydrin being present in at least an equimolar amount to the molar amount of the total of carboxyl and hydroxyl groups of gallic acid and dehydrohalogenation of the resulting halohydrin ether and halohydrin ester moieties in an aqueous solution of an alkali metal hydroxide, with the amount of the alkali metal hydroxide being at least 1 times the molar amount of the total of hydroxyl groups and carboxyl group of the gallic acid, in the presence of said phase transfer catalyst at 20° to 30° C. to give a product mixture containing polyglycidyl compounds having the general formula:

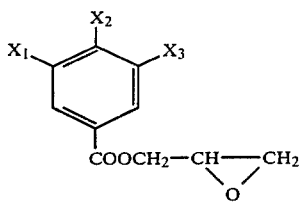

wherein $X_1$, $X_2$ and $X_3$ are —OH or

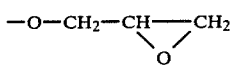

provided that at least one of $X_1$ to $X_3$ is

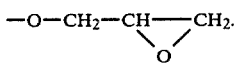

2. The epoxy resin of claim 1, wherein during the reaction of the gallic acid and the epihalohydrin, the epihalohydrin is present in an amount of 3 to 10 times the molar amount of the total of the carboxyl and hydroxy groups of gallic acid and during the dehydrohalogenation the amount of the alkali metal hydroxide is 1.3 to 2.5 times the molar amount of the total of the hydroxyl groups and the carboxyl group of the gallic acid.

3. An epoxy resin produced by reaction of tannic acid and an epihalohydrin in the presence of a phase transfer catalyst and in the substantial absence of water at 50° to 110° C., with the epihalohydrin being present in at least an equimolar amount to the molar amount of the total of carboxyl and hydroxyl groups of tannic acid and dehydrohalogenation of the resulting halohydrin ether and halohydrin ester moieties in an aqueous solution of an alkali metal hydroxide, with the amount of the alkali metal hydroxide being at least 1 times the molar amount of the total of hydroxyl groups and carboxyl groups of the tannic acid, in the presence of said phase transfer catalyst of 20° to 30° C. to give a product mixture containing polyglycidyl compounds having the general formula:

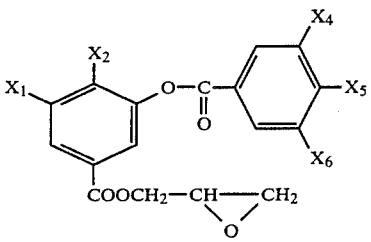

wherein $X_1$, $X_2$, $X_4$, $X_5$ and $X_6$ are —OH or

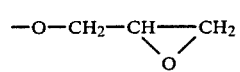

provided that at least one of $X_1$, $X_2$, $X_4$, $X_5$ and $X_6$ is

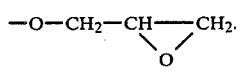

4. The epoxy resin of claim 3, wherein during the reaction of the tannic acid and the epihalohydrin, the epihalohydrin is present in an amount of 3 to 10 times the molar amount of the total of the carboxyl and hydroxyl groups of tannic acid and during the dehydrohalgenation, the amount of the alkali metal hydroxide is 1.3 to 2.5 times the molar amount of the total of the hydroxyl groups and the carboxyl group of the tannic acid.

* * * * *